(12) United States Patent
Alzona et al.

(10) Patent No.: US 11,754,574 B2
(45) Date of Patent: Sep. 12, 2023

(54) RED CELL DILUENT WITH EDTA AND METHODS FOR MAKING AND USING THE SAME

(71) Applicant: Immucor, Inc., Norcross, GA (US)

(72) Inventors: Mortimer Alzona, Norcross, GA (US); Bryan Marshall, Norcross, GA (US); Elizabeth Cope, Norcross, GA (US); Margot Borgel, Norcross, GA (US); Teresa Welch, Norcross, GA (US)

(73) Assignee: IMMUCOR, INC., Norcross, GA (US)

( * ) Notice: Subject to any disclaimer, the term of this patent is extended or adjusted under 35 U.S.C. 154(b) by 786 days.

(21) Appl. No.: 16/500,713

(22) PCT Filed: Apr. 3, 2018

(86) PCT No.: PCT/US2018/025918
§ 371 (c)(1),
(2) Date: Oct. 3, 2019

(87) PCT Pub. No.: WO2018/187348
PCT Pub. Date: Oct. 11, 2018

(65) Prior Publication Data
US 2020/0191806 A1    Jun. 18, 2020

Related U.S. Application Data

(60) Provisional application No. 62/480,879, filed on Apr. 3, 2017.

(51) Int. Cl.
*G01N 33/80* (2006.01)
*G01N 1/38* (2006.01)
*G01N 33/50* (2006.01)
*G01N 33/68* (2006.01)

(52) U.S. Cl.
CPC ............. *G01N 33/80* (2013.01); *G01N 1/38* (2013.01); *G01N 33/5005* (2013.01); *G01N 33/6854* (2013.01)

(58) Field of Classification Search
CPC ............. G01N 33/80; G01N 33/5005; G01N 33/6854; G01N 1/38
See application file for complete search history.

(56) References Cited

U.S. PATENT DOCUMENTS

2002/0022271 A1* 2/2002 Ryan ................. G01N 33/5094
422/50
2010/0178656 A1* 7/2010 Buffiere .............. G01N 33/537
435/7.1
2012/0294798 A1   11/2012 Nelson et al.

OTHER PUBLICATIONS

Hartmann et al. Investigating thr Role of Surface Materials and Three Dimensional Architecture on In Vitro Differentiation of Porcine Monocyte-Derived Dendritic Cells. PLOS ONe 11 (6): e0158503 pp. 1-19 (Jun. 30, 2016).*

(Continued)

*Primary Examiner* — Gailene Gabel
(74) *Attorney, Agent, or Firm* — COZEN O'CONNOR

(57) ABSTRACT

The present disclosure relates to a red blood cell (RBC) solution comprising ethylenediaminetetraacetic acid (EDTA) and methods for making and using the same. The solution can comprise EDTA at a concentration from 3-5 g/L, including 4 g/L. Well plates prepared using the solution can provide a decreased rate of false positive results in automated immunoassays for detecting RBC antibodies in a patient sample.

10 Claims, 3 Drawing Sheets

(56) References Cited

OTHER PUBLICATIONS

Banfi et al. The role of ethylenediamine tetraacetic acid (EDTA) as in vitro anticoagulant for diagnostic purposes. Clin. Chem. Lab. Med. 45 (5): 565-576 (2007).*

Arias et al. (Jun. 2010) "Red Blood Cell Permeabilization by Hypotonic Treatments, Saponin, and Anticancer Avicins", Biochimica et Biophysica Acta (BBA)—Biomembranes, 1798(6):1189-1196.

Banfi et al. (2007) "The Role of Ethylenediamine Tetraacetic Acid (EDTA) as in Vitro Anticoagulant for Diagnostic Purposes", Clinical Chemistry and Laboratory Medicine, 45(5):565-576.

Musawi et al. (May 2016) "In Vitro Mean Red Blood Cell Volume Change Induced by Diode Pump Solid State Low-Level Laser of 405nm", Photomedicine and Laser Surgery, 34(5):211-214.

International Search Report issued in International Application No. PCT/US2018/025918 dated Jul. 20, 2018, 5 pages.

* cited by examiner

RED CELL DILUENT WITH EDTA AND METHODS FOR MAKING AND USING THE SAME

CROSS-REFERENCE TO RELATED APPLICATIONS

This application is a national stage entry of PCT Application No. PCT/US2018/025918, filed Apr. 3, 2018, which claims priority to U.S. Provisional Application for Patent Ser. No. 62/480,879, filed Apr. 3, 2017, the entire contents of which are incorporated herein by reference.

FIELD OF THE DISCLOSURE

The present disclosure relates to the use of ethylenediaminetetraacetic acid (EDTA) as a component in a red cell diluent (RCD) for the preparation of capture plates for immunoassays. The present disclosure also relates to assays using such plates.

BACKGROUND OF THE DISCLOSURE

Prior to receiving a transfusion involving RBCs (i.e., human RBCs), a patient must be tested for the presence of antibodies against specific RBC antigens, especially those that may cause unwanted reactions in the recipient. Exemplary immunoassays include a hemagglutination reaction in a microtiter based format, including a solid-phase assay. In such methods, microtiter wells contain fragments of RBCs that have been immobilized to the well surface using a linking agent. The RBC fragments display antigens that serve as the capture component of the assay.

As patient samples are added to the wells, any antibodies present within the sample that have a specificity to the red blood cell antigens which are immobilized on the well surface, bind to those antigens. After a series of washing steps, indicator cells (e.g., antibody-coated RBCs) are then added to the well. Indicator cells bind to any antibodies bound to the well. After incubation, the wells are centrifuged. Any unbound indicator cells centrifuge to the center of the well and form a visible pellet. Bound cells remain bound to the well and prevent the formation of a distinct pellet.

The absence of a distinct pellet is interpreted as a positive result whereas the formation of a pellet is interpreted as a negative result. The pellet size and shape can impact the determination from negative through positive with varying degrees of reactivity.

Such assays can be performed manually or with automated systems. Automated systems increase the speed in performing the immunoassays, but can have unexpected positive reactions with negative samples. Negative samples (i.e., samples absent of red blood cell antibodies) can result in positive or equivocal (undetermined) reactions. Such results can require further testing and unnecessarily searching for an alternate donor. There remains a need for an automated immunoassay with a decreased rate of false positive results.

SUMMARY OF THE DISCLOSURE

The present disclosure relates to a RBC solution comprising ethylenediaminetetraacetic acid (EDTA), for example, disodium EDTA and/or tetrasodium EDTA. Well plates prepared using an EDTA-containing RBC solution can provide a decreased rate of false positive results in automated hemagglutination assays.

Described herein are methods of preparing a RBC solution by providing RBCs and suspending the RBCs in a solution comprising EDTA. The solution can comprise EDTA at a concentration from 3-5 g/L, including 4 g/L.

Also described herein are methods of preparing a well, for example, wells in a 96-well plate. A well can be prepared by providing RBCs; suspending the RBCs in a solution comprising EDTA; providing a well comprising a RBC attachment molecule bound to a surface of the well; applying RBC solution to the well to bind RBCs to the RBC attachment molecule, thereby immobilizing RBCs in the well; treating the well with a RBC lysing agent; and washing the well; and treating the well with a drying solution (e.g., a desiccant), wherein the prepared well comprises RBC fragments, such as RBC membranes and/or RBC stroma. The present disclosure also relates to wells prepared by these methods.

The present disclosure also relates to methods for detecting RBC antibodies by providing the well prepared according to the disclosed methods, contacting the well with a sample comprising RBC antibodies, and detecting RBC antibodies bound to RBC fragments in the well. Also disclosed herein are kits for detecting RBC antibodies that comprise the well prepared according to the disclosed methods.

DETAILED DESCRIPTION

In the manufacture of well-plates for hemagglutination assays, RBCs can be used to form a cell monolayer attached to the well surface. Red blood cells are sourced as whole or packed cell units from donor centers. Units are washed and resuspended in a buffered red cell storage solution (known as red cell diluent, or RCD). When the RBCs are ready to be used for the manufacture of well-plates, the red cells can be resuspended to a specific concentration (as measured by hematocrit) in RCD.

Ethylenediaminetetraacetic acid (EDTA) can be added to the RCD (RCD containing EDTA, "ERCD") prior to plating. The EDTA can be, for example, disodium EDTA and/or tetrasodium EDTA. This dilutes (i.e., bulks) the RBCs prior to plating. Including EDTA in the RCD can result in coated well-plates that have reduced rates of unexpected false positive/equivocal assay results, including in automated assays.

The RBC solutions (i.e., RBCs suspended in RCD) disclosed herein can comprise EDTA in the RCD at a concentration of about 3-5 g/L. For example, EDTA can be included at a concentration of about 3 g/L, at about 4 g/L, or about 5 g/L. The EDTA can be included at 3 g/L, 4 g/L, or 5 g/L. The EDTA can be included at 3.0 g/L, 3.1 g/L, 3.2 g/L, 3.3 g/L, 3.4 g/L, 3.5 g/L, 3.6 g/L, 3.7 g/L, 3.8 g/L, 3.9 g/L, 4.0 g/L, 4.1 g/L, 4.2 g/L, 4.3 g/L, 4.4 g/L, 4.5 g/L, 4.6 g/L, 4.7 g/L, 4.8 g/L, 4.9 g/L, or 5.0 g/L.

Methods of preparing such a RBC solution can comprise providing RBCs and suspending the RBCs in a solution comprising EDTA. The EDTA can be, for example, disodium EDTA and/or tetrasodium EDTA. EDTA can be included in the solution at the above-identified concentrations.

Wells, such as in a microtiter well-plate or a microtiter well-strip, can be prepared by providing or preparing the EDTA-containing RBC solution described herein. An attachment molecule can be incubated in a well so that it adheres to the well surface. After incubation, the well can be washed to remove excess unbound material. Washing can manual or automated. The EDTA-containing RBC solution can be added to the well and allowed to incubate, for example, overnight, to allow adhesion of the RBCs to the well surface, via the attachment molecule.

Figure 3:
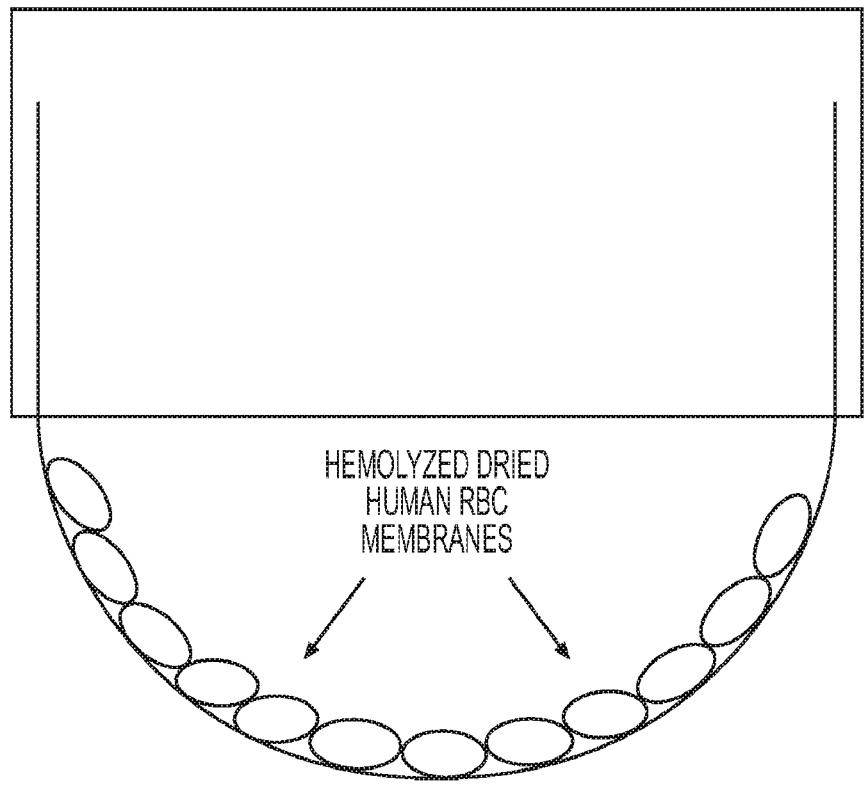
FIG. 3 shows a microtiter well coated with human RBC membranes prepared in accordance with the methods described herein.

Next, a lysing solution can be added to the well to lyse the RBCs. The wells can be washed to remove cellular debris. Only bound cell fragments containing specific antigens, for example, antigens to antibodies whose presence are to be identified in a patient sample, including IgG antibodies, can remain in the well. A drying solution can be added to the wells prior to further packaging or storage. After a curing period, for example, at least or about three days, the well-plate can be stored at ambient temperature. FIG. 3 shows a prepared well.

Wells, well-plates, and/or well-strips prepared in accordance with the methods described herein can be included in a kit for detecting RBC antibodies. The kit can include additional elements required for the assay, such as indicator cells.

Wells or well-plates prepared in accordance with the methods described herein can be used in methods for detecting RBC antibodies, including manual and automated methods. The methods can include steps of providing the wells or well-plates described herein, contacting the well with a sample comprising RBC antibodies, and detecting RBC antibodies bound to RBC fragments in the well. The sample can be a biological sample containing antibodies to RBC antigens, such as a blood, plasma, or serum sample. The biological sample can be treated with other substances, such as anti-coagulants, needed to preserve the sample for the time period between obtaining the sample from a patient and testing the sample. The sample can be obtained from a patient requiring a blood transfusion, for example, a patient who is to be tested for the presence of antibodies, including alloantibodies to RBC antigens.

Figure 1:
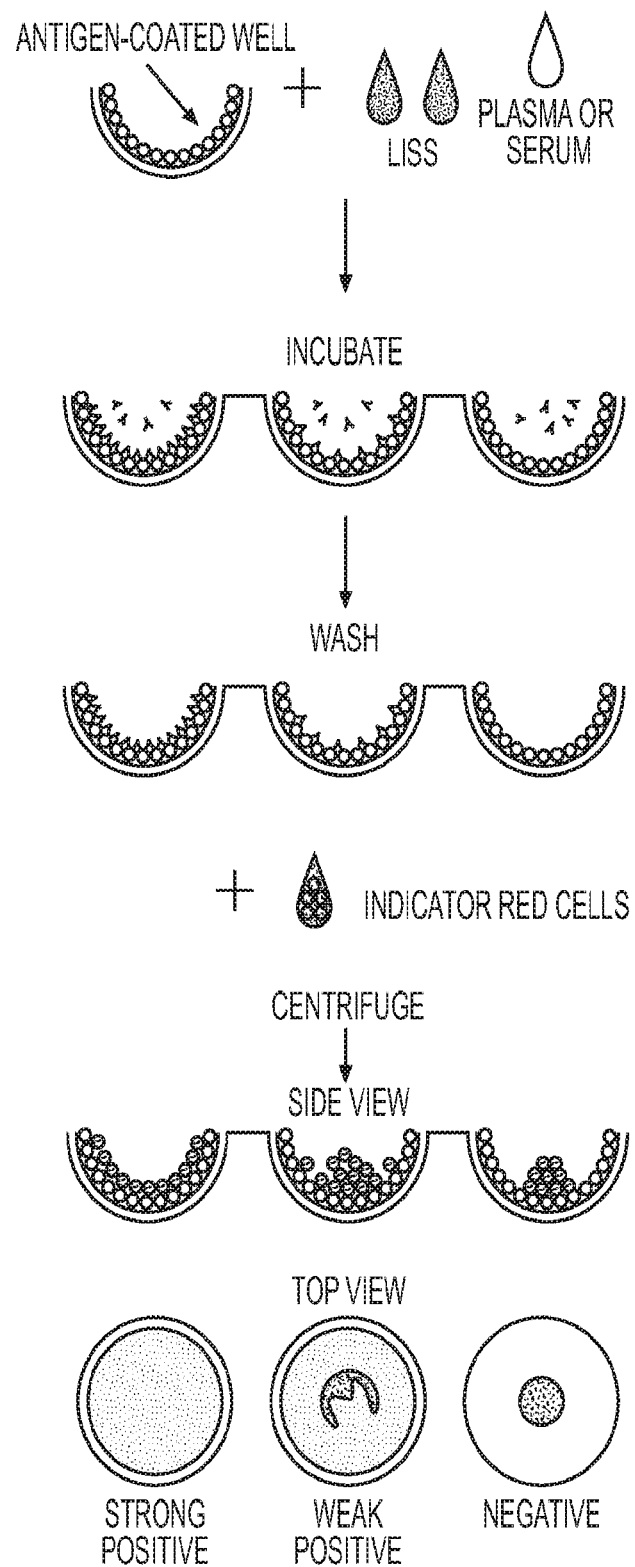
FIG. 1 shows the steps of an immunoassay to detect the presence of RBC antibodies.

FIG. 1 shows exemplary steps of the detection methods. In the detection methods, any antibodies present within the sample that have a specificity to the RBC antigens that are immobilized on the well surface, can bind to those antigens. Such antibodies can include antibodies typically tested in hemagglutination assays. Such antibodies can include IgG antibodies, for example, clinically significant IgG antibodies. Such antibodies can include antibodies associated with hemolytic disease of the newborn. Such antibodies can include Kidd antibodies (including anti-$Jk^a$ and anti-$Jk^b$), Kell antibodies (including anti-K), and/or MNS antibodies (including anti-S).

The antigen-coated well, which is prepared in accordance with the method described above, is provided. To test for RBC antibodies, such as IgG antibodies, a patient plasma or serum sample can added to the well, optionally, with a low ionic strength saline (LISS) solution to increase the amount of antibody taken up by the RBC cells or RBC fragments in the well during subsequent sensitization. An exemplary LISS solution can comprise glycine, bromcresol purple dye and sodium azide as a preservative. After an incubation period, the wells can be washed one or more times to remove unbound antibodies.

Indicator cells can then be added to the wells to detect bound antibodies. The indicator cells can be antibody-coated RBCs, such as RBCs coated with an anti-IgG antibody. The indicator cells can be in the form of a suspension of red blood cells coated with murine monoclonal anti-human IgG molecules. Indicator cells can bind to any antibodies bound to the well (e.g., antibodies bound to the RBC cell monolayer coating the well).

The wells or plate can then be centrifuged. When the wells are then centrifuged, the IgG/Anti-IgG binding will prevent the indicator cells from migrating to the bottom of the well—if antibody was bound during the incubation phase. Any unbound indicator cells can centrifuge to the center of the well and form a visible pellet. Bound cells can remain bound to the well and can prevent the formation of a distinct pellet.

Figure 2:
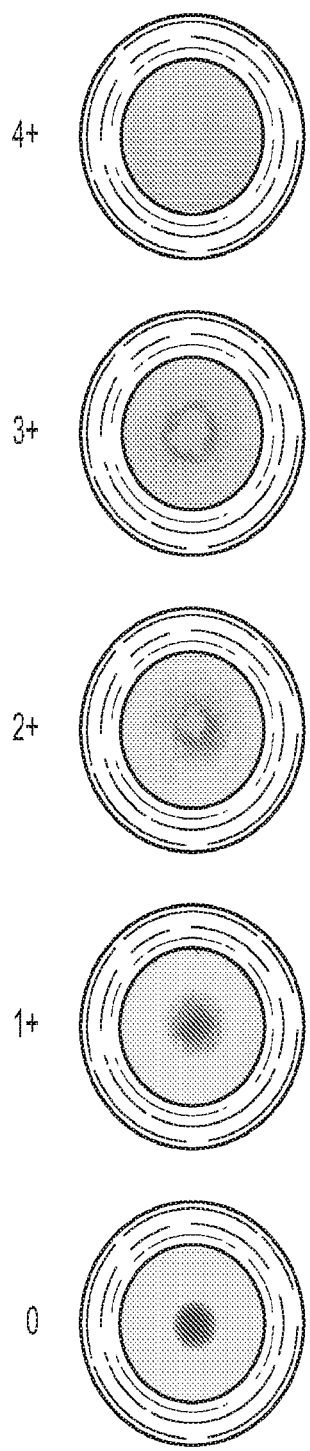
FIG. 2 shows a grading chart for automated RBC antibody detection using wells and plates prepared according to the present disclosure.

Automated detection systems can be used to perform the detection method. The absence of a distinct pellet can be interpreted as a positive result (4+ in FIG. 2) and the formation of a pellet can be interpreted as a negative result (0 in FIG. 2). The pellet size and shape can impact the determination from negative through positive with varying degrees of reactivity (1+ through 3+ in FIG. 2). The rate of unexpected false positive/equivocal assay results can be reduced in such methods. Automated systems and assays can involve machine detection and scoring of hemaagglutination reactions (i.e., pellet/reactivity scoring). Exemplary automated systems include the Echo®, Galileo®, and NEO® systems of Immucor®.

The assays and kits disclosed herein can also use or include positive and negative control reagents. An exemplary positive control reagent can comprise antibodies to red blood cells. An exemplary negative control reagent contains no antibodies to red blood cells.

EXAMPLES

The following examples are offered by way of illustration and not by way of limitation.

Example 1—Preparation of RBC-EDTA Solutions

Red blood cells are sourced as whole or packed cell units from donor centers. Prior to plating, the units are prepared for plating by washing and resuspending them in a red cell storage solution (red cell diluent, or RCD) that includes disodium EDTA at a concentration of 4 g/L.

Example 2—Preparation of Well Plate 96-well polystyrene plates or 8-well polystyrene strips are added to an automation line where an attachment molecule is added to each well. The attachment molecule is incubated to allow adhesion to the well surface and then excess and unbound material is washed away. RBCs from the solution prepared in Example 1 are then added to each well and allowed to incubate overnight to allow adhesion of the red cells to the well surface (via the attachment molecule).

Subsequent to overnight incubation, a lysing solution is added to each well to lyse the red cells. Wells are washed and cellular debris is removed leaving only the bound cell fragments containing specific red cell antigens. A drying solution is added to the plates and the plates are packaged and stored in a cooler for a minimum of three days to allow further "curing" of the product. The plates are then stored at ambient temperature.

Example 3—Assay

The well-plate or strip of Example 2 can be used in an immunoassay to detect RBC antibodies using automated equipment. A patient plasma sample and LISS are added to the wells in the well-plate. The sample is incubated in the wells so that IgG antibodies present within the sample that have a specificity to the red blood cell antigens that are immobilized on the well surface, bind to those antigens. The wells are washed one or more times.

Indicator cells (RBCs coated with anti-IgG antibody) are added to the well. Indicator cells bind to any antibodies bound to the well. After incubation, the wells are centrifuged. Any unbound indicator cells centrifuge to the center of the well and form a visible pellet. Bound cells remain bound to the well and would prevent the formation of a distinct pellet. The automated equipment determines the results from negative through positive with varying degrees of reactivity. There is a lower rate of false positive rates in the assay using the plates prepared in accordance with Example 2 than with conventional plates.

Example 4—Kit and Assay

A kit is provided comprising the well-plate or strip of Example 2, LISS solution, and indicator red cells. A patient serum or plasma sample is provided. All reagents and the patient sample(s) are brought to 18-30° C. Two drops (100+/−10 uL) of the LISS solution is added to each well. One drop (50±5 uL) of the test serum/plasma is added to each well.

The wells are incubated at 36-38° C. for 15-60 minutes. The sample-LISS mixture is decanted or aspirated from the wells. The wells are washed with saline. One drop (50±5 uL) of indicator red cells are added to each well. The wells are centrifuged for 1-3 minutes at 450-600×g. After centrifugation, the wells are examined for the adherence or the absence of indicator red cell adherence, either manually or using automated equipment, and scored, for example, using the scale shown in FIG. 2.

While the foregoing disclosure provides some detail for purposes of clarity and understanding, it will be appreciated by one skilled in the art from a reading of this disclosure that various changes in form and detail can be made without departing from the true scope of the invention and appended claims. All patents and publications cited herein are entirely incorporated herein by reference.

The invention claimed is:

1. A method of preparing a well comprising:
preparing a RBC solution by suspending packed red blood cells (RBCs) in a solution comprising ethylenediaminetetraacetic acid (EDTA); and
applying the RBC solution to a well to allow the RBCs in the RBC solution to attach to the surface of the well, thereby immobilizing RBCs in the well, and
treating the immobilized RBCs with a lysing agent such that fragments of the RBCs remain immobilized in the well.

2. The method of claim 1, wherein the well comprises an attachment molecule bound to a surface of the well and the RBCs are immobilized in the well by the attachment molecule.

3. The method of claim 1, further comprising washing the well to remove cellular debris.

4. The method of claim 3, further comprising treating the well with a drying solution.

5. The method of claim 4, wherein the well is stored for at least three days following treatment with the drying solution.

6. The method of claim 1, wherein the treating with the lysing agent is performed at least twenty-four hours after applying the RBC solution to the well.

7. The method claim 1, wherein the well surface comprises polystyrene.

8. The method of claim 1, wherein the solution comprises EDTA at a concentration from 3-5 g/L.

9. The method of claim 8, wherein the concentration is 4 g/L.

10. The method of claim 1, wherein the EDTA is one or more of disodium EDTA and tetrasodium EDTA.

* * * * *